United States Patent [19]

Deshpande et al.

[11] Patent Number: 5,034,219
[45] Date of Patent: Jul. 23, 1991

[54] PRE-PERM HAIR CONDITIONER

[75] Inventors: Vikas M. Deshpande, Ringwood, N.J.; John M. Walts, Shohola, Pa.

[73] Assignee: Sterling Drug Inc., Rensselaer, N.Y.

[21] Appl. No.: 322,759

[22] Filed: Mar. 13, 1989

[51] Int. Cl.$^5$ .......................... A61K 7/06; A61K 7/08
[52] U.S. Cl. ........................ 424/71; 424/70; 424/78; 132/202
[58] Field of Search .............. 424/70, 71, 78; 132/202

[56] References Cited

U.S. PATENT DOCUMENTS

| Re. 31,126 | 1/1983 | Dasher et al. | 132/7 |
|---|---|---|---|
| 3,423,504 | 1/1969 | Birkelo et al. | 424/70 |
| 3,912,808 | 10/1975 | Sokol | 424/71 |
| 4,144,326 | 3/1979 | Luedicke, Jr. et al. | 424/70 |
| 4,175,572 | 11/1979 | Hsiung et al. | 132/7 |
| 4,269,824 | 5/1981 | Villamarin et al. | 424/70 |
| 4,275,055 | 6/1981 | Nachtigal et al. | 424/70 |
| 4,421,740 | 12/1983 | Burton | 424/70 |
| 4,445,521 | 5/1984 | Grollier et al. | 132/7 |
| 4,612,188 | 9/1986 | Zorayan et al. | 424/47 |
| 4,638,822 | 1/1987 | Grollier et al. | 132/7 |
| 4,658,839 | 4/1987 | Dallal et al. | 132/7 |
| 4,719,104 | 1/1988 | Patel | 424/70 |

Primary Examiner—Thurman Page
Assistant Examiner—Amy Hulina
Attorney, Agent, or Firm—John R. Everett

[57] ABSTRACT

A hair conditioning composition which when applied to color-treated hair prior to perming with formulations based on thioglycolate or sulfite minimizes the reduction in tensile strength of the hair comprising about 0.1 to about 4.0 weight-percent of a water-dispersible dialkyl ($C_{12-18}$) dimethyl ammonium halide; about 0.1 to about 2.5 weight-percent of alkyl ($C_{12-18}$) dimethyl benzyl ammonium halide; about 0.1 to about 2.0 weight-percent of a homopolymer of diallyl dialkyl ammonium halide; optionally a thickener, a moisturizer, an emulsifier, a protein conditioner, a preservative, a colorant, and/or a perfume; and the remainder to 100 weight-percent water; and a method of conditioning color-treated hair therewith.

8 Claims, No Drawings

PRE-PERM HAIR CONDITIONER

BACKGROUND OF THE INVENTION

1. Field of the Invention

The invention relates to a composition for conditioning hair and more specifically to such a composition which, when applied to chemically damaged hair, such as color-treated hair, prior to permanent waving with perming compositions based on thioglycolate or sulfite reducing agents, minimizes damage to the hair by reducing the lose of tensile strength of the hair.

2. Information Disclosure Statement

The straightening and waving or perming of hair with compositions based on thioglycolate or sulfite reducing agents has enjoyed popularity for some time. One problem however which often results from the use of such compositions is that the hair sustains chemical damage due to loss in tensile strength of the hair fibers, a consequence of which is that the hair then tends to undergo significant further deterioration. In an attempt to correct this, certain conditioners have been suggested or used for application to the hair either prior or subsequent to perming or as a component of the perming composition itself. Although the use of such conditioners has met with varying degrees of success, considerable room exists for improvement.

U.S. Pat. No. 3,423,504 discloses aqueous creme hair rinse compositions containing a N-benzyl higher fatty alkyl dilower-alkyl quaternary ammonium halide and a higher fatty acid amide and which additionally may contain a higher fatty alcohol such as cetyl alcohol or a higher fatty ester.

U.S. Pat. No. 4,144,326 discloses aqueous creme rinse compositions for conditioning hair containing a combination of two quaternary ammonium compounds, i.e., dodecyl trimethyl ammonium chloride and dimethyl dialkyl ammonium chloride, and a thickener.

U.S. Pat. No. 4,445,521 discloses compositions for treating hair, skin and nails which comprise a cationic polymer in combination with an anionic polymer. The cationic polymer may be a homopolymer of dialkyl diallyl ammonium chloride.

U.S. Pat. No. 4,269,824 discloses aqueous after shampoo hair conditioner compositions comprising a dimethyl di(hydrogenated tallow) ammonium salt, a quaternized hydrolyzed collagen protein, a cationic quaternized polymer of hydroxyethylcellulose, and a mixture of long chain alcohols containing at least 90% by weight of $C_{16}$ and $C_{18}$ alcohols in a 1 to 2 weight ratio. The composition additionally may include a thickener, e.g., hydroxyethylcellulose.

U.S. Pat. No. 4,275,055 discloses hair conditioning compositions including as conditioning agents stearyl dimethyl benzyl ammonium chloride and stearimidopropyl dimethyl benzyl ammonium chloride.

U S. Pat. No. 4,421,740 discloses aqueous hair conditioning compositions consisting essentially of a quaternary conditioning agent and cetyl alcohol in specifically defined ratios, a protective colloid and water. Various quaternary compounds which are suitable are disclosed including stearyl dimethyl benzyl ammonium chloride and di(hydrogenated tallow) dimethyl ammonium chloride.

U.S. Pat. No. 4,612,188 discloses compositions for treating keratin substances such as hair, skin and nails, containing a certain bis-(quaternary ammonium) compound having two lipophilic chains. One exemplified composition is a pre-shampoo lotion which additionally contains a homopolymer of dimethyl diallyl ammonium chloride.

U.S. Pat. No. 4,638,822 discloses a process for setting hair which in a first stage consists of applying to the hair at least one cationic polymer and at least one anionic polymer in a solvent medium. Among the quaternary ammonium polymers which can be used is mentioned the homopolymer of dimethyl diallyl ammonium chloride.

U.S. Pat. No. 31,126, reissue of U.S. Pat. No. 4,061,150, discloses a method of treating hair by first treating the hair with an aqueous composition containing certain types of quaternary ammonium compounds which are substantive to hair and thereafter washing the hair with a shampoo containing an anionic detergent. Quaternary ammonium compounds which may be employed include those containing at least one long chain aliphatic hydrocarbon attached to the nitrogen such as dodecyl dimethyl benzyl ammonium chloride and stearyl dimethyl benzyl ammonium chloride.

U.S. Pat. No. 3,912,808 discloses aqueous compositions for waving or straightening hair containing a reducing agent and an amine polymer or a polymer of dialkyl diallyl ammonium salts.

U.S. Pat. No. 4,175,572 discloses aqueous hair conditioner compositions for use under highly alkaline conditions comprising mineral oil, a C12–18 fatty alcohol, a nonionic emulsifier, and a quaternary ammonium polymer which may be a homopolymer having recurring units of dialkyl diallyl ammonium salts.

SUMMARY OF THE INVENTION

It has been unexpectedly discovered that when color-treated hair is conditioned with an aqueous composition containing a combination of three cationic quaternary ammonium compounds in specific amounts prior to waving or straightening of the hair with compositions based on thioglycolate or sulfite reducing agents, the reduction of tensile strength of and hence damage to the hair which normally results from treatment with thioglycolate or sulfite based compositions is significantly reduced.

Thus in one aspect the invention provides a pre-waving or pre-straightening hair conditioning composition which comprises by weight of the composition:

(a) from about 0.1 to about 4.0 percent of a water-dispersible dialkyl dimethyl ammonium halide where alkyl has from 12 to 18 carbon atoms;

(b) from about 0.1 to about 2.5 percent of a water-dispersible alkyl dimethyl benzyl ammonium halide where alkyl has from 12 to 18 carbon atoms;

(c) from about 0.1 to about 2.0 percent of a water-soluble homopolymer of dialkyl diallyl ammonium halid comprising recurring units of the formula:

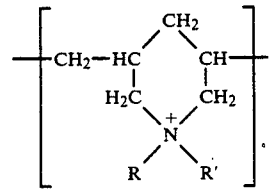

wherein R and R' independently of one another are alkyl having from 1 to 3 carbon atoms; and (d) the remainder to 100 percent water.

In another aspect the invention provides a method for conditioning color-treated hair in order to minimize the loss of tensile strength of the hair fibers which normally results from the straightening or waving of hair with formulations based on thioglycolate or sulfite reducing agents which method comprises applying to the hair prior to treatment with said formulations the pre-waving or prestraightening hair conditioning composition defined hereinabove, allowing the composition to remain in contact with the hair for from about 5 to about 20 minutes and rinsing the hair.

The method of the invention, particularly when employed to condition color-treated hair, results in improved tensile strength properties of the hair subsequent t waving or straightening of the hair with thioglycolate or sulfitebased formulations.

DETAILED DESCRIPTION OF THE INVENTION INCLUDING THE PREFERRED EMBODIMENTS

The composition of the invention comprises in specific amounts four essential ingredients as follows: two water-dispersible cationic surface active agents, a water-soluble cationic polymer of a dialkyl diallyl ammonium salt, and water. The combination of the two cationic surface active agents and the cationic polymer is a conditioner for the hair and is essential to provide improved tensile strength properties to the hair fibers. Although only the essential ingredients are required in order to practice the invention, the composition preferably additionally contains one or more adjuvants in order to provide thereto beneficial properties as described more fully hereinbelow.

CATIONIC SURFACE ACTIVE AGENTS

The composition contains two cationic surface active agents.

The first cationic surface active agent is a water-dispersible quaternary ammonium compound which is dialkyl dimethyl ammonium halide

$$(R)_2 \overset{+}{N}(CH_3)_2 X^- \qquad I$$

wherein R is straight or branched chain alkyl having 12; to 178 carbon atoms and $X^-$ is halide, particularly chloride or bromide, chloride being preferred. Mixtures of these compounds may be employed. Illustrative examples of such compounds are dicoco dimethyl ammonium chloride, di(hydrogenated tallow) dimethyl ammonium chloride, didodecyl dimethyl ammonium chloride, dihexadecyl dimethyl ammonium chloride and dioctadecyl dimethyl ammonium chloride. A particularly preferred compound is di(hydrogenated tallow) dimethyl ammonium chloride. The compound of formula I is employed in the composition of the invention in a concentration of from about 0.1 to about 4.0 percent by weight of the composition, preferably from about 0.8 to about 2.4 percent by weight.

The second cationic surface active agent is a water-dispersible quaternary ammonium compound which is an alkyl dimethyl benzyl ammonium halide represented by the formula:

$$R_1 R_2 \overset{+}{N}(CH_3)_2 X^- \qquad II$$

wherein $R_1$ is a straight or branched alkyl having from 12 to 18 carbon atoms, $R_2$ is benzyl and $X^-$ is halide, particularly chloride or bromide, chloride being preferred. Mixtures of these compounds may be employed. Illustrative examples of such compounds are dodecyl dimethyl benzyl ammonium chloride, tetradecyl dimethyl benzyl ammonium chloride and octadecyl dimethyl benzyl ammonium chloride. A particularly preferred compound is octadecyl dimethyl benzyl ammonium chloride. The compound of formula II is employed in the composition of the invention in a concentration of from about 0.1 to about 2.5 percent by weight of the composition, preferably from about 0.4 to about 1.5 weight percent.

Compounds of formulas I and II and procedures for their preparation are well known in the art.

CATIONIC POLYMER

The cationic polymer is a water-soluble dialkyl diallyl ammonium halide homopolymer having an average molecular weight of from about 20,000 to about 3,000,000 containing, as the main constituents of the chain, units corresponding to the following formula:

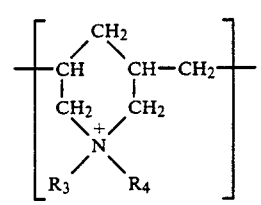

where $R_3$ and $R_4$ independently of one another are alkyl having from 1 to 3 carbon atoms. The homopolymers of formula III are described in U.S. Pat. No. 3,912,808 and can be prepared as described in U.S. Pat. No. 3,288,770, each patent incorporated herein by reference. These homopolymers are employed in a concentration of from about 0.1 to about 2.0 percent by weight of the composition, a preferred concentration being from about 0.3 to about 1.2 percent by weight.

OPTIONAL INGREDIENTS

In addition to the essential ingredients of the composition of the invention, there may be included optional ingredients in order to impart thereto additional beneficial properties and/or to improve the aesthetic value thereof such as thickeners, moisturizers, emulsifiers, additional hair conditioners, preservatives, colorants and perfumes or fragrances.

Thickeners which may be used dry for example water-soluble gums such as the cellulose gums, illustrative examples of which are methylcellulose, ethyloellulose, hydroxymethylcellulose, hydroxyethylcellulose and hydroxypropylmethylcellulose. It is advantageous to employ a thickener to build up the viscosity of the composition in order to facilitate application thereof to the hair and to ensure good adherency to the hair during the required contact period. The amount of thickener which can be employed will depend on the particular thickening agent and the degree of thickening desired. The cellulose gums generally will be used in an amount of from 0.1 to 2 percent by weight of the composition.

Moisturizers may be selected from any of those well known in the cosmetic art. Among those which may be mentioned are the ethoxylated and propoxylated glucose derivatives such as the polyethylene glycol or polypropylene glycol ethers of methyl glucose with 10 or 20 ethylene oxide or propylene oxide units. The moisturizer generally will be used in an amount of from 0.1 to 5 percent by weight of the composition.

Emulsifiers which may be employed are those of the nonionic type such as polyethyleneated, polypropyleneated and polyglycerolated fatty alcohols and alkylphenols, ethylene oxide/propylene oxide copolymers, fatty acid esters of glycerol and sorbitol and mono- and di- fatty acid esters of polyethylene glycol having 400 to 6000 ethylene oxide units. The amounts used generally will be from 1 to 20 percent by weight of the composition.

There may also be included in the composition of the invention a protein conditioner such as a derivative of hydrolyzed animal protein, e.g., oleamidopropyl dimethyl amine hydrolyzed animal protein (CTFA adopted name). The amounts employed will generally be from 0.1 to 5 percent by weight of the composition.

Any of the well known antimicrobial agents used to preserve cosmetic compositions may be incorporated such as methylparaben, ethylparaben, propylparaben, chloroallyl methenamine chloride, methylchloroisothiazolone and methylisothiazolone, 1,3-dimethylol-5,5-dimethyl hydantoin, imidazolinyl urea and benzyl alcohol. Such agents are used in antimicrobially effective amounts.

The composition of the invention is preferably applied to damp hair immediately after shampooing with a conventional shampoo. The composition is worked into and evenly distributed throughout the hair and then is left in contact with the hair for from about 5 to about 20 minutes after which the hair is rinsed free of residuals.

The hair then may be waved or straightened using conventional techniques and waving and straightening sulfite- or thioglycolate-containing compositione. Although the composition of the invention can be left in contact with the hair longer than 20 minutes no advantage is gained in doing so and excessive contact times may hinder to some extent the rupture of the disulfide linkages in the keratin fibers during the perming process.

The compositions of the invention, when formulated without optional emulsifiers and thickeners, can be prepared by adding the ingredients in any order to water with suitable mixing at ambient temperature. However, heating is required if emulsifiers and thickeners are to be included. A convenient procedure, when thickeners, moisturizers and emulsifiers are to be incorporated, is as follows:

(1) add the total formula amount of water into a first stainless steel manufacturing kettle and commence high speed agitation;

(2) slowly sprinkle the thickening agent(s) into the water with constant high speed agitation until a clear solution is formed;

(3) commence heating with moderate agitation to 70°-75° C.;

(4) add the two cationic surface active agents, the homopolymer of dialkyl diallyl ammonium halide and the moisturizing agent(s);

(5) add to a second stainless steel manufacturing kettle the emulsifying agent(s) and heat to 70°-75° C. with slow agitation to melt the emulsifiers(s);

(6) with both manufacturing kettles at 70°-75° C., slowly transfer the melt from the second kettle into the first kettle with moderate agitation and mix for about 15-20 minutes using sidewall scrapers; start cooling with moderate agitation and, if a protein conditioner is to be included, add this ingredient at 45°-50° C.;

(8) add any perfume and preservative at 40° C. and continue cooling and agitation until 30° C.; and (9) stop cooling and agitation and allow the composition to come to ambient temperature.

The composition of the invention is illustrated by the following example without, however, being limited thereto.

The weight-percent figures in the following example denote 100% active ingredient.

EXAMPLE 1

HAIR CONDITIONING LOTION

| Ingredient | Weight-Percent |
|---|---|
| Homopolymer of dialkyl diallyl ammonium halide[1] | 0.40 |
| Stearyl dimethyl benzyl ammonium chloride[2] | 0.60 |
| Di(hydrogenated tallow) dimethyl ammonium chloride[3] | 1.35 |
| Hydroxyethylcellulose[4] | 1.10 |
| Polypropylene glycol (10 units) methyl glucose ether[5] | 0.50 |
| Glyceryl stearate[6] | 4.00 |
| Polyethylene glycol (12 units) distearate[7] | 4.00 |
| Cetyl alcohol | 1.50 |
| Stearyl alcohol | 8.00 |
| Protein conditioner[8] | 0.34 |
| Preservative[9] | 0.40075 |
| Perfume | 0.30 |
| Dye (D&C Yellow No. 10) | 0.30 |
| Water (deionized) q.s. to | 100% |
| pH 4.2 | |

[1] Merquat 100, available from Merck & Co., Inc., a 40% aqueous solution of the homopolymer of dimethyl diallyl ammonium chloride having an average molecular weight of $10^5$-$10^6$ (CTFA Adopted Name: Polyquaternium-6).
[2] Ammonyx 4, available from Onyx Chemical Company as a 20% active material in 75% water/5% stearyl/cetyl alcohol vehicle.
[3] Varisoft DHT, available from Sherex Chemical Company as a 75% active material in aqueous isopropanol.
[4] Natrosol HHR 250 (100% active), available from Hercules, Inc.
[5] Glucam P-10 (100% active), available from Amerchol Corporation; conforms to the formula

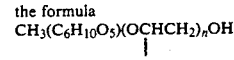

where n has an average value of 10 (CTFA Adopted Name: PPG-10 Methyl Glucose Ether).
[6] Cerasynt SD (100% active), available from Van Dyk & Company, Inc.
[7] Kessco PEG 600 Distearate (100% active), available from Stepan Chemical Company (CTFA ADopted Name: PEG-12 Distearate).
[8] Lexein CP-125, available from Inolex Chemicals as an 48% active aqueous liquid; the active ingredient is the amine salt of oleamidopropyl dimethylamine and Hydrolyzed Animal Protein (DTFA Adopted Name: Oleamidopropyl Dimethyl Hydrolyzed Animal Protein).
[9] 0.40% Benzyl alcohol plus 0.00075% of a mixture of methylchloroisothiazolone and methylisothiazolone available from Rohm and Haas Company, Inc. under the name Kathon CG as a 1.5% active aqueous solution.

The hair conditioning lotion of Example 1 is a viscous liquid having a yellowish opaque appearance.

EXAMPLE 2

A hair conditioning lotion was prepared identical in all respects to that of Example 1 except that no dye was used and only Kathon CG was used as preservative in an amount to provide 0.0015 weight-percent active. The lotion is a viscous liquid having a white opaque appearance.

Tests were conducted to compare the reduction in tensile strength of both color-treated hair and normal (not colored-treated) hair after treatment with (1) the composition of Example 1 of the invention, (2) a commercial pre-perming conditioning formulation (Composition A), followed immediately in each case by treatment with a commercial hair perming formulation (Composition B); (3) in the case of the color-treated hair, a commercial hair perming formulation (Composition C) designed for color-treated hair, and (4) in the case of the normal hair, a commercial formulation (Composition D) designed for normal hair, both Compositions C and D having hair conditioners incorporated therein and intended for use without pre-treatment of the hair with a hair conditioning agent.

Compositions B, C and D comprise two formulations each for sequential application, the first a hair waving lotion with reducing agent and the second a neutralizer.

| Composition A | |
|---|---|
| Ingredient | Weight-Percent[1] |
| Sodium Lauryl Sulfate | 2.20 |
| Hydrolyzed Animal Protein[2] | 0.50 |
| Potassium Cocoate | 2.56 |
| Spermwax | 8.00 |
| Cetyl Alcohol | 11.50 |
| Lanolin, Anhydrous | 0.80 |
| Ozokerite 1140[3] | 0.36 |
| Petrolatum, White | 6.84 |
| Perfume | 0.59 |
| Quaternium-15[2,4] | 0.20 |
| Water, Deionized | q.s. to 100% |

[1] Based on 100% active.
[2] CTFA Adopted Name; manufactured by Stepan Chemical Company under the name of Polypeptide 37.
[3] Blend of high amount of branched chain hydrocarbon waxes with a lower percentage of straight chain hydrocarbon waxes; sold by Frank B. Ross Co., Inc.
[4] N-(3-chloroallyl)hexaminium chloride (preservative).

| Composition B | |
|---|---|
| Waving Lotion Ingredient | Neutralizer Ingredient |
| Ammonium Hydroxide | Methylparaben |
| Thioglycolic Acid[1] | Quaternium-52[2,4] |
| Potassium Coco-Hydrolyzed Animal Protein[2] | Cetearyl Alcohol[2,5] |
|  | Ceteth-20[2,6] |
| Lanolin Oil | Sodium Lauryl Sulfate |
| Cloud K3906[3] | Hydrogen Peroxide[7] |
| Lanolin, Anhydrous | Disodium Phosphate |
| Water, Deionized | Phosphoric Acid |
|  | Fragrance |
|  | Water, Deionized |

[1] 5.90 Weight-Percent.
[2] CTFA Adopted Name.
[3] A mixture of mineral oil, potassium oleate, ethylene glycol and the polyethylene glycol (average of 23 units) ether of lauryl alcohol (CTFA Adopted Name: Laureth-23).
[4] Quaternary ammonium salt conforming to the general formula:

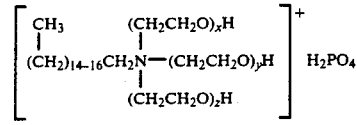

wherex+y+z has an average value of 10.
[5] Mixture of fatty alcohols consisting predominantly of cetyl and stearyl alcohols.
[6] Polyethylene glycol (average of 20 units) ether of cetyl alcohol.
[7] 2.38 Weight-Percent

| Composition C | |
|---|---|
| Waving Lotion[1] | Neutralizer |
| Ingredient | Ingredient |
| Ethanolamine Thioglycolate[2] | Hydrogen Peroxide[6] |
| Ethanolamine | Laureth-23[3,4] |
| Laureth-23[3,4] | Quaternium-18[3,7] |
| Mineral Oil | Fragrance |
| Polyquaternium-16[5] | Water |
| Potassium Oleate | pH 2.81 |
| Ethylene Glycol | |
| Oleic Acid | |
| D&C Red No. 27 | |
| Isopropyl Myristate | |
| Fragrance | |
| Water | |

[1] Formulated as an aerosol with hydrofluorocarbon 152A as propellant and sodium silicate as corrosion inhibitor.
[2] Amount equivalent to 5.19 weight-percent of thioglycolic acid.
[3] CTFA Adopted Name.
[4] Polyethyleneglycol (average of 23 units) ether of lauryl alcohol.
[5] Copolymer of methyl vinyl imidazolium chloride and vinyl pyrrolidone.
[6] 1.3 Weight-Percent
[7] Di(hydrogenated tallow) dimethyl ammonium chloride.

Composition D

Waving Lotion

Same ingredients as for Composition C except that the amount of ethanolamine thioglycolate is equivalent to 5.10 weight-percent of thioglycolic acid.

Neutralizer

Same as for Composition C except that the pH is 3.26.

Hair Treatment Procedures

In Procedures 1 to 3 which follow, the shampoo used was the same.

Procedure 1 a. Shampoo: immersion in 10% shampoo solution—2 min.
b. Rinse: immersion in warm tap water—5 times
c. Pre-Perm conditioner: coat each hair—15 min.
d. Rinse: immersion in warm tap water—5 times
e. Waving Lotion: total immersion—25 min.
f. Rinse: immersion in warm tap water—5 times
g. Neutralizer: total immersion—5 min.
h. Rinse: immersion in warm tap water—5 times
i. Return to sample bottle in deionized water Procedure 2 a. Shampoo: immersion in 10% shampoo solution—2 min.
b Rinse: immersion in warm tap water—5 times
c. Waving Lotion: completely cover with foam—30 min.
d. Rinse: immersion in warm tap water—5 times
e. Cover hair with plastic cap for 15 min.
f. Neutralizer: total immersion—5 min.
g. Rinse: immersion in warm tap water—5 times
h. Return to sample bottle in deionized water Procedure 3 a. Shampoo: immersion in 10% shampoo solution—2 min.
b. Rinse: immersion in warm tap water—5 times
c. Waving Lotion: total immersion—35 min.
d. Rinse: immersion in warm tap water—5 times
e. Leave hair covered with plastic cap for 15 min.
f. Neutralizer: total immersion—5 min.
g. Rinse: immersion in warm tap water—5 times h. Return to sample bottle in deionized water Procedure 1 was used for pre-conditioning hair samples with the composition of Example 1 and Composition A and subsequent treatment of the conditioned hair samples with the waving lotion and neutralizer of Composition B. Procedures 2 and 3 were used for treating hair samples with the waving lotion and neutralizer of Compositions C and D respectively. In all cases, immediately after completion of the procedure, the tensile strength of each hair sample was measured.

Procedure For Selecting Hair Samples and Testing Tensile Strength

I. Color Treated Hair

1. An Instron Model 4201 was programmed for the following parameters and these conditions were maintained throughout all the tests:

Elongation limit- 14.00 mm
c. Crosshead speed- 50.00 mm/min.
d. Load Cell- 5 g

2. A single bundle of European dark brown hair was color treated twice with L'Oreal Ultimate Natural Blonde Hair Color. Two hundred hair fibers were removed and tagged 1-200. The hair fibers were then placed into individual bottles of deionized water and equilibrated for 24 hours prior to initial tensile strength evaluation.

3. Hair with peak load values between 37.5 and 47.5 gf were selected for treatment and testing. One hundred (100) hairs were in this group. The hair fibers were divided into four groups of twenty-five (25) hairs each by a random sampling.

4. The hair fibers were again equilibrated for 24 hours in deionized water before they wer treated in accordance with the appropriate hair treatment procedure described hereinabove.

5. The groups of hair were coded to identify the pre-perm conditioner and/or the waving lotion/neutralizer with which they were treated.

II. Normal Hair

Steps 1, 4 and 5 are as for I above. Steps 2 and 3 are as follows:

2. One hundred fifty (150) individual European dark brown hair fibers were removed from a single bundle and tagged 1-150. The hair fibers were placed into individual bottles of deionized water and equilibrated for 24 hours prior to initial tensile strength evaluation.

3. Hair with peak load values between 38.85 and 51.85 gf were selected for treatment and testing. Seventy-five (75) hairs were in this group. The hair fibers were divided into three groups of twenty-five (25) hairs each by a random sampling.

Results of Tensile Strength Test

The percent change in tensile strength (hereafter TS) was calculated for each hair. The values from each group were evaluated in a paired t test to determine the statistical significance between groups at 95% confidence level.

1. Hair fibers (color-treated) treated with the composition of Example 1 compared to those treated with Composition A, with subsequent treatment with Composition B in each case, gave the following results:

|  | Average % Change in TS | Standard Deviation |
| --- | --- | --- |
| Example 1/Comp. B | −35.7844 | 9.62818 |
| Comp. A/Comp. B | −42.9608 | 12.2311 |

The Calculated t Value is 2.30515 and the Critical t Value is 2.0 for 48 Degrees of Freedom and a 95% Confidence Level. Therefore there is a difference in the tensile strength of the hair fibers treated with Example 1/Composition B and those treated with Composition A/Composition B, i.e., hair fibers treated with Example 1 showed less of a loss of tensile strength than those treated with Composition A.

2. Hair fibers (color-treated) with the composition of Example 1 with subsequent treatment with Composition B compared to those treated with Composition C gave the following results:

|  | Average % Change in TS | Standard Deviation |
| --- | --- | --- |
| Example 1/Comp. B | −35.7844 | 9.62818 |
| Comp. C | −56.3212 | 11.8678 |

The Calculated t Value is 5.93017 and the Critical Value is 2.021 for 40 Degrees of Freedom and a 95% Confidence Level. Eight (8) hair fibers treated with Composition C broke during the final tensile test and were excluded from the statistical analysis. These results show there is a difference in the tensile strength of the hair fibers treated with Example 1/Composition B and those treated with Composition C, i.e., hair fibers treated with Example 1/Composition B showed less of a loss of tensile strength than those treated with Composition C.

3. Hair fibers (normal) treated with the composition of Example 1 compared to those treated with Composition A, with subsequent treatment with Composition B in each case, gave the following results:

|  | Average % Change in TS | Standard Deviation |
| --- | --- | --- |
| Example 1/Comp. B | −16.0412 | 14.0350 |
| Comp. A/Comp. B | −9.70545 | 4.67303 |

The Calculated t Value is 2.12711 and the Critical t Value is 2.013 for 45 Degrees of Freedom and a 95% Confidence Level. Three hair fibers treated with Composition A/Composition B broke during the final tensile test and were excluded from the statistical analysis. These results show that there is a difference in the tensile strength of the hair fibers treated with Example 1/Composition B compared to those treated with Composition A/Composition B, i.e., hair fibers treated with Example 1/Composition B showed a greater loss of tensile strength than those treated with Composition A/Composition B.

4. Hair fibers (normal) treated with the composition of Example 1 with subsequent treatment with Composition B compared to those treated with Composition D gave the following results:

|  | Average % Change in TS | Standard Deviation |
| --- | --- | --- |
| Example 1/Comp. B | −16.0412 | 14.035 |

|  | Average % Change in TS | Standard Deviation |
|---|---|---|
| Composition D | −18.0604 | 14.7009 |

The Calculated t Value is 0.496733 and the Critical t Value is 2.01 for 48 Degrees of Freedom and a 95% confidence Level. Therefore there is no difference in the tensile strength of hair fibers treated with Example 1/Composition B as compared to those treated with Composition D.

The foregoing tests establish that pre-conditioning of color-treated hair with the composition of the invention provides significantly better protection against reduction of tensile strength of the hair during perming than either Composition A, a pre-conditioner, or Composition C, a perming system specifically formulated so as not to require pre-conditioning.

We claim:

1. A pre-waving or pre-straightening hair conditioning composition which comprises by weight of the composition:
   (a) from about 0.1 to about 4.0 percent of a water-dispersible dialkyl dimethyl ammonium halide where alkyl has from 12 to 18 carbon atoms;
   (b) from about 0.1 to about 2.5 percent of a water-dispersible alkyl dimethyl benzyl ammonium halide where alkyl has from 12 to 18 carbon atoms;
   (c) from about 0.1 to about 2.0 percent of a water-soluble homopolymer of dialkyl diallyl ammonium halide having an average molecular weight of 20,000 to 3,000,000 comprising recurring units of the formula:

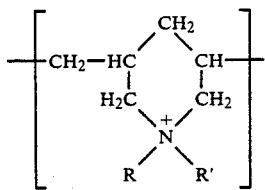

wherein R and R' independently of one another are alkyl having from 1 to 3 carbon atoms; and
   (d) the remainder to 100 percent water.

2. The composition of claim 1 which comprises about 0.8 to about 2.4 percent of the dialkyl dimethyl ammonium halide; from about 0.4 to about 1.5 percent of the alkyl dimethyl benzyl ammonium halide; about 0.3 to about 1.2 percent of the homopolymer of dialkyl diallyl ammonium halide; and the remainder to 100 percent water.

3. The composition of claim 2 which comprises:
   (a) about 1.35 percent of the dialkyl dimethyl ammonium halide;
   (b) about 0.6 percent of the alkyl dimethyl benzyl ammonium halide;
   (c) about 0.4 percent of the homopolymer of dialkyl diallyl ammonium halide; and
   (d) the remainder to 100 percent water.

4. The composition of claim 1 which comprises:
   (a) from about 0.1 to about 4.0 percent of di(hydrogenated tallow) dimethyl ammonium halide;
   (b) from about 0.1 to about 2.5 percent of stearyl dimethyl benzyl ammonium halide;
   (c) from about 0.1 to about 2.0 percent of the homopolymer of dimethyl diallyl ammonium halide having an average molecular weight of $10^5$ to $10^6$; and
   (d) the remainder to 100 percent water.

5. The composition of claim 4 which comprises:
   (a) from about 0.8 to about 2.4 percent of di(hydrogenated tallow) dimethyl ammonium halide;
   (b) from about 0.4 to about 1.5 percent of stearyl dimethyl benzyl ammonium halide;
   (c) from about 0.3 to about 1.2 percent of the homopolymer of dimethyl diallyl ammonium halide having an average molecular weight of $10^5$ to $10^6$; and
   (d) the remainder to 100 percent water.

6. The composition of claim 5 which comprises:
   (a) about 1.35 percent of di(hydrogenated tallow) dimethyl ammonium halide;
   (b) about 0.6 percent of stearyl dimethyl benzyl ammonium halide;
   (c) about 0.4 percent of the homopolymer of dimethyl diallyl ammonium halide having an average molecular weight of $10^5$ to $10^6$; and
   (d) the remainder to 100 percent water.

7. The composition of claim 6 consisting essentially of about 1.35 percent of di(hydrogenated tallow) dimethyl ammonium chloride; about 0.6 percent of stearyl dimethyl benzyl ammonium chloride; about 0.4 percent of the homopolymer of dimethyl diallyl ammonium chloride having an average molecular weight of $10^5$ to $10^6$; about 1.1 percent of hydroxyethylcellulose, about 1.5 percent of propylene glycol (10 units) methyl glucose ether; about 4 percent of glyceryl stearate; about 4 percent of polyethylene glycol (12 units) distearate; about 1.5 percent of cetyl alcohol; about 8 percent of stearyl alcohol; about 0.34 percent of a protein conditioner; an effective amount of a preservative; and the remainder to 100 percent water.

8. A method for conditioning color-treated hair in order to minimize the loss of tensile strength of the hair fibers which normally results from the straightening or waving of hair with formulations based on thioglycolate or sulfite reducing agents which method comprises applying to the hair prior to treatment with said formulations the pre-waving or pre-straightening hair conditioning composition of claim 1, allowing the composition to remain in contact with the hair for from about 5 to about 20 minutes and rinsing the hair.

* * * * *

UNITED STATES PATENT AND TRADEMARK OFFICE
CERTIFICATE OF CORRECTION

PATENT NO. : 5,034,219
DATED : July 23, 1991
INVENTOR(S) : Vikas M. Deshpande and John M. Walts It is certified that error appears in the above-identified patent and that said Letters Patent is hereby corrected as shown below:

Abstract, "diallyl dialkyl" should read --dialkyl diallyl--.

Column 12, lines 13 & 31, "105 to 106" should read --$10^5$ to $10^6$--.

Column 12, line 39, "1.5" should read --0.5--.

Signed and Sealed this

Fifth Day of January, 1993

*Attest:*

DOUGLAS B. COMER

*Attesting Officer*   Acting Commissioner of Patents and Trademarks